US00PP36732P2

(12) United States Plant Patent
Wood

(10) Patent No.: US PP36,732 P2
(45) Date of Patent: Jun. 10, 2025

(54) ***VIBURNUM* PLANT NAMED 'SMNVCST'**

(50) Latin Name: *Viburnum carlesii*
Varietal Denomination: SMNVCST

(71) Applicant: Timothy D. Wood, Spring Lake, MI (US)

(72) Inventor: Timothy D. Wood, Spring Lake, MI (US)

(73) Assignee: SPRING MEADOW NURSERY, INC., Grand Haven, MI (US)

( * ) Notice: Subject to any disclaimer, the term of this patent is extended or adjusted under 35 U.S.C. 154(b) by 0 days.

(21) Appl. No.: 18/947,816

(22) Filed: Nov. 14, 2024

(51) Int. Cl.
*A01H 5/00* (2018.01)
*A01H 6/86* (2018.01)

(52) U.S. Cl.
USPC ..... Plt./226

(58) Field of Classification Search
USPC ..... Plt./226
See application file for complete search history.

(56) References Cited

U.S. PATENT DOCUMENTS

PP24,251 P2 * 2/2014 Wood ..... A01H 6/00
Plt./226

* cited by examiner

*Primary Examiner* — Karen M Redden
(74) *Attorney, Agent, or Firm* — C. Anne Whealy

(57) ABSTRACT

A new and distinct cultivar of *Viburnum* plant named 'SMNVCST', characterized by its relatively compact, upright, mounding and outwardly spreading tree-form habit; vigorous growth habit; freely branching habit; leaves that turn vibrant red and yellow green in the autumn; large dense inflorescences with numerous fragrant white-colored flowers; and good container and garden performance.

5 Drawing Sheets

Figure 1:
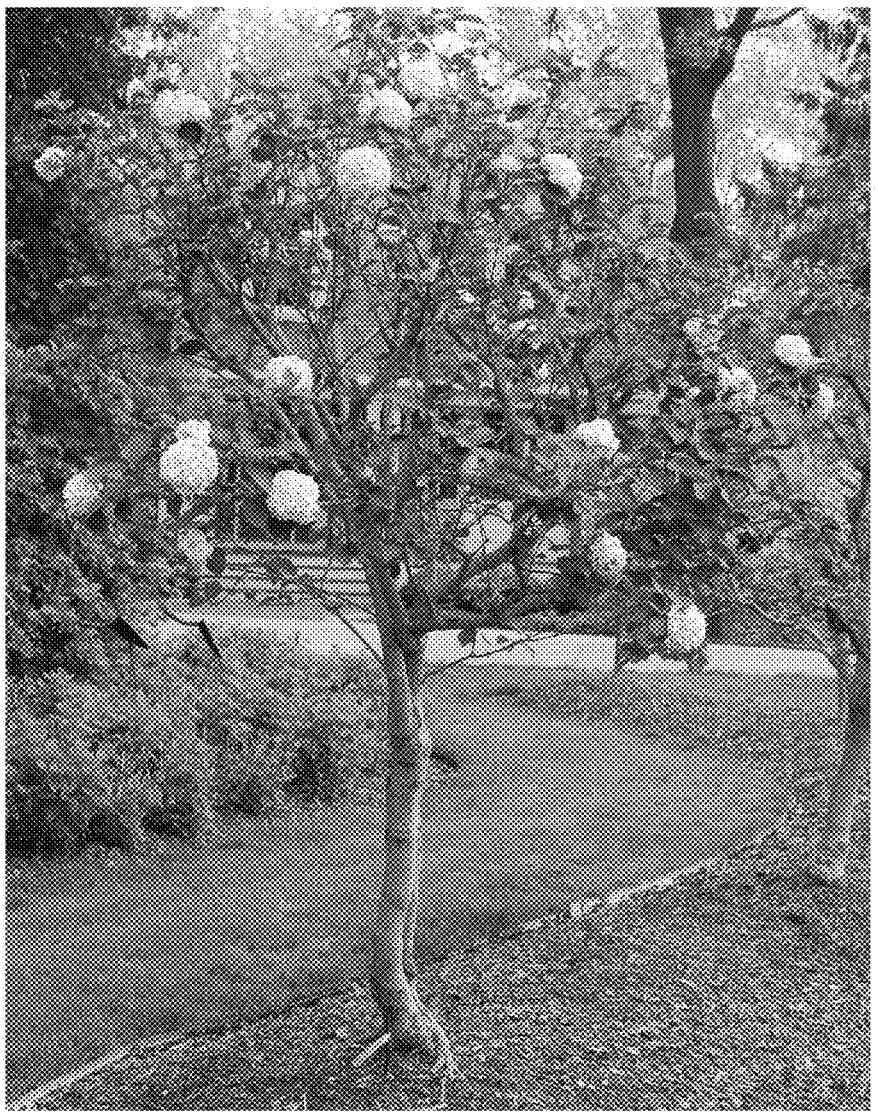

Botanical designation: *Viburnum carlesii.*
Cultivar denomination: 'SMNVCST'.

BACKGROUND OF THE INVENTION

The present invention relates to a new and distinct cultivar of *Viburnum* plant, botanically known as *Viburnum carlesii*, commonly referred to as Koreanspice *Viburnum* and hereinafter referred to by the name 'SMNVCST'.

The new *Viburnum* plant is a product of a planned breeding program conducted by the Inventor in Grand Haven, Michigan. The objective of the breeding program is to develop new tree-form *Viburnum* plants with large and fragrant inflorescences.

The new *Viburnum* plant originated from an open-pollination in 2013 of *Viburnum carlesii* 'Diana', not patented, as the female, or seed, parent with an unknown selection of *Viburnum carlesii* as the male, or pollen, parent. The new *Viburnum* plant was discovered and selected by the Inventor in 2016 as a single flowering plant from within the progeny of the stated open-pollination in a controlled environment in Grand Haven, Michigan.

Asexual reproduction of the new *Viburnum* plant by softwood cuttings in a controlled environment in Grand Haven, Michigan since 2016 has shown that the unique features of this new *Viburnum* plant are stable and reproduced true to type in successive generations of asexual reproduction.

SUMMARY OF THE INVENTION

Plants of the new *Viburnum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNVCST'. These characteristics in combination distinguish 'SMNVCST' as a new and distinct *Viburnum* plant:

1. Relatively compact, upright, mounding and outwardly spreading tree-form habit.
2. Vigorous growth habit.
3. Freely branching habit.
4. Leaves that turn vibrant red and yellow green in the autumn.
5. Large dense inflorescences with numerous fragrant white-colored flowers.
6. Good container and garden performance.

Plants of the new *Viburnum* can be compared to plants of the female parent, 'Diana'. Plants of the new *Viburnum* differ primarily from plants of 'Diana' in the following characteristics:

1. Inflorescences of plants of the new *Viburnum* are larger and denser than inflorescences of plants of 'Diana'.
2. Flowers of plants of the new *Viburnum* are white in color whereas flowers of plants of 'Diana' are light pink in color.

Plants of the new *Viburnum* can be compared to plants of the *Viburnum carlesii* 'Spiro', disclosed in U.S. Plant Pat. No. 24,251. Plants of the new *Viburnum* differ primarily from plants of 'Spiro' in the following characteristics:

1. Plants of the new *Viburnum* have larger leaves than plants of 'Spiro'.
2. Plants of the new *Viburnum* have larger inflorescences than plants of 'Spiro'.

3. Flowers of plants of the new *Viburnum* are white in color whereas flowers of plants of 'Spiro' are light pink and white in color.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet (FIG. 1) is a side perspective view of a typical flowering plant of 'SMNVCST' grown in a garden.

Figure 2:
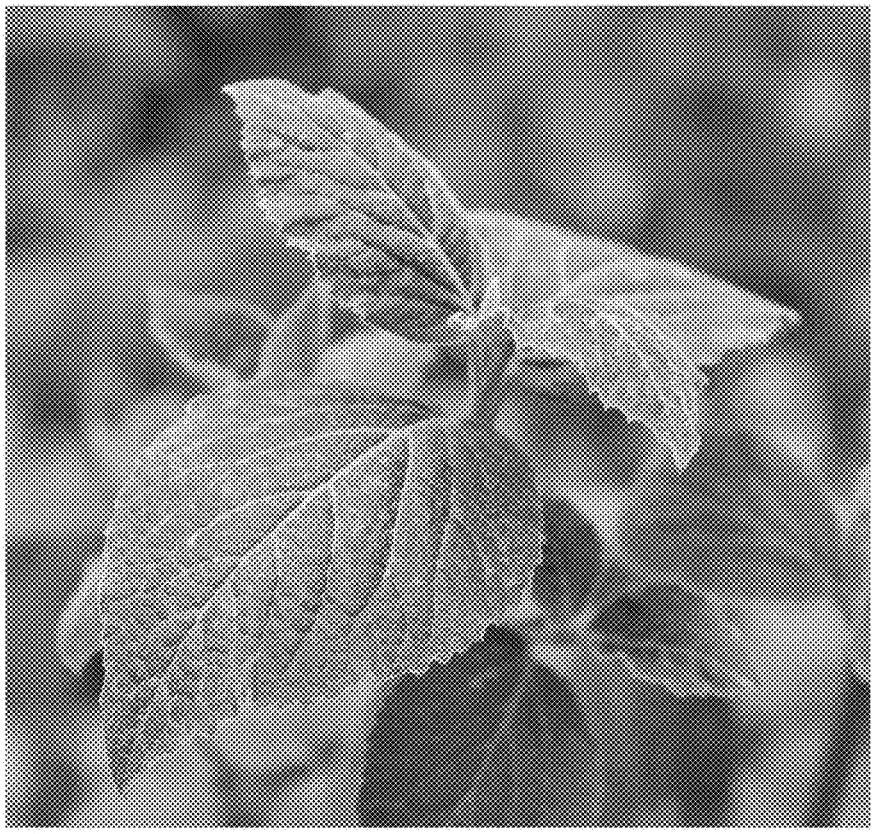

The photograph on the second sheet (FIG. 2) is a close-up view of typical developing leaves of 'SMNVCST'.

Figure 3:
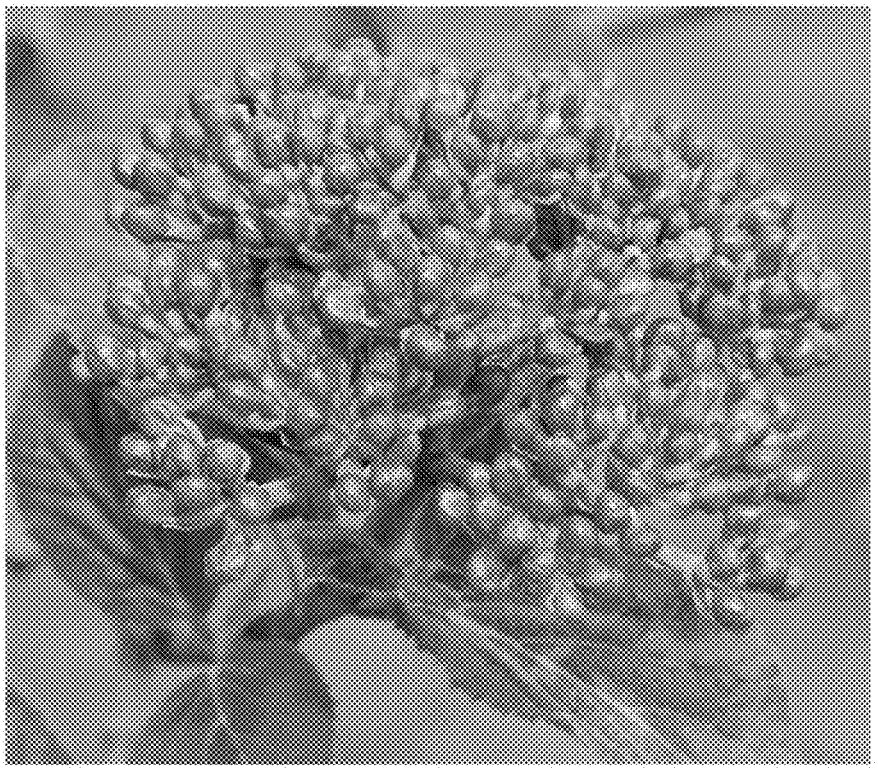

The photograph on the third sheet (FIG. 3) is a close-up view of a typical developing inflorescence of 'SMNVCST' in bud.

Figure 4:
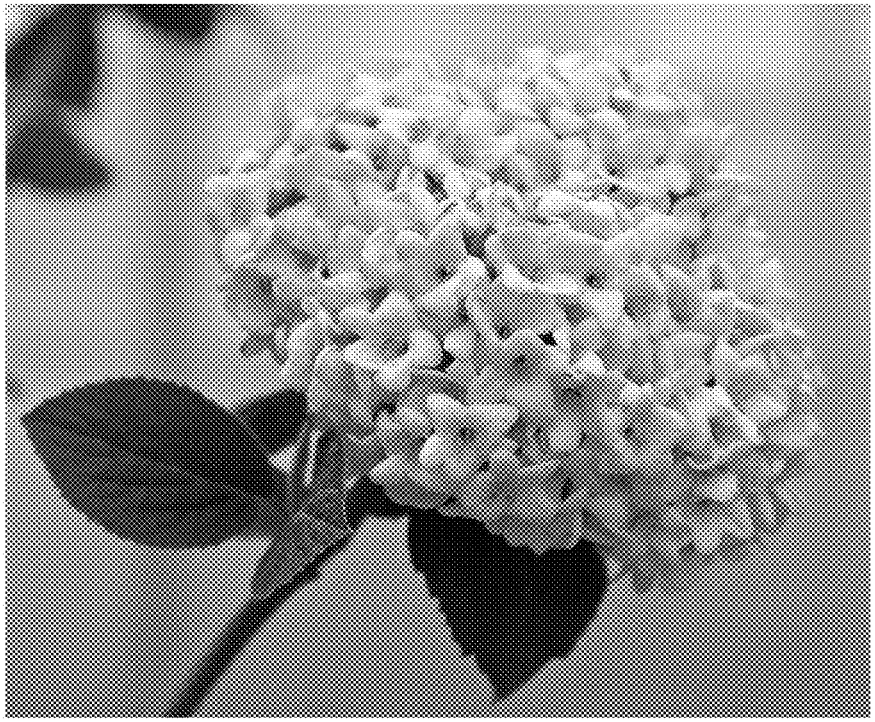

The photograph on the fourth sheet (FIG. 4) is a close-up view of a typical inflorescence of 'SMNVCST' with open flowers.

Figure 5:
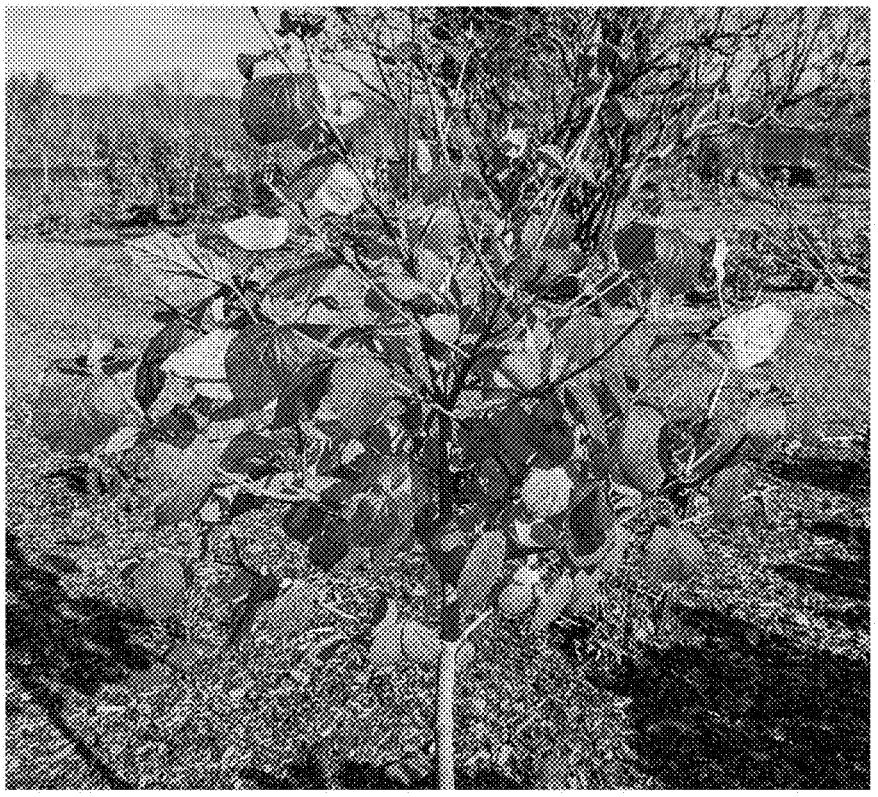

The photograph on the fifth sheet (FIG. 5) is a side perspective view of a typical plant of 'SMNVCST' grown in the garden in the autumn.

DETAILED BOTANICAL DESCRIPTION

The aforementioned photographs and following observations, measurements and values describe plants of the new *Viburnum* grown in seven-gallon containers during the spring in a polypropylene-covered shadehouse in Grand Haven, Michigan and under cultural practices typical of commercial *Viburnum* production. During the production of the plants, day temperatures ranged from 18° C. to 27° C. and night temperatures ranged from ranged from 5° C. to 10° C. Plants were eight years old when the photographs were taken and seven years old when the detailed description was taken. In the description, color references are made to The Royal Horticultural Society Colour Chart, 1995 Edition, except where general terms of ordinary dictionary significance are used.

Botanical classification: *Viburnum carlesii* 'SMNVCST'.

Parentage:

*Female, or seed, parent.*—*Viburnum carlesii* 'Diana', not patented.

*Male, or pollen, parent.*—Unknown selection of *Viburnum carlesii*, not patented.

Propagation:

*Type.*—By softwood cuttings.

*Time to initiate roots, summer.*—About 20 days at temperatures about ranging from about 18° C. to 27° C.

*Time to produce a rooted young plant, summer.*—About three months at temperatures ranging from about 18° C. to 27° C.

*Root description.*—Fine to thick, fibrous; typically white in color, actual color of the roots is dependent on substrate composition, water quality, fertilizer, substrate temperature and physiological age of roots.

*Rooting habit.*—Freely branching; dense.

Plant description:

*Plant and growth habit.*—Perennial shrub; relatively compact, upright, mounding and outwardly spreading tree-form habit; vigorous growth habit and moderate growth rate.

*Branching habit.*—Freely branching habit with about 12 to 15 lateral branches developing per plant.

*Plant height.*—About 190 cm.

*Plant diameter* (*area of spread*).—About 120 cm.

Lateral branch description:

*Length.*—About 92.6 cm.

*Diameter.*—About 2.1 cm.

*Internode length.*—About 9 cm.

*Texture.*—Pubescent, pubescence canescent; becoming woody with development.

*Strength.*—Strong.

*Aspect.*—About 45° to 80° from vertical.

*Color, developing.*—Close to 144B.

*Color, when woody.*—Close to N199C; canescent pubescence, close to 199C.

Leaf description:

*Arrangement.*—Opposite, simple.

*Length.*—About 10 cm.

*Width.*—About 6 cm.

*Shape.*—Elliptic.

*Apex.*—Acute to broadly acuminate.

*Base.*—Cuneate.

*Margin.*—Serrate.

*Texture, upper surface.*—Pubescent; rough.

*Texture, lower surface.*—Pubescent; prominent venation.

*Venation pattern.*—Pinnate.

*Color.*—Developing leaves, upper surface: Close to NN137C. Developing leaves, lower surface: Close to N138C. Fully expanded leaves, upper surface: Close to NN137B; venation, close to 144B. Fully expanded leaves, lower surface: Close to 146B; venation, close to 144B. Autumn, upper and lower surfaces: Close to 180A and 150C.

*Petioles.*—Length: About 1.5 cm. Diameter: About 2 mm. Texture, upper and lower surfaces: Slightly pubescent. Color, upper and lower surfaces: Close to 144B.

Flower description:

*Flower appearance and arrangement.*—Single salver-form flowers arranged in terminal compound cymes; freely flowering habit with typically about 180 to 200 flowers developing per inflorescence; flowers face upright to outwardly depending on position in the inflorescence.

*Natural flowering season.*—Plants of the new *Viburnum* flower in April and May in Michigan; flowers not persistent.

*Fragrance.*—Strongly fragrant; sweet and slightly peppery; hyacinth-like.

*Flower buds.*—Length: About 7 mm. Diameter: About 4 mm. Shape: Spatulate. Color: Close to 144C variably blushed with close to 174A to 174B.

*Inflorescence height.*—About 6 cm.

*Inflorescence diameter.*—About 10 cm.

*Flower diameter.*—About 1.2 cm.

*Flower length* (*height*).—About 9 mm.

*Flower throat diameter.*—About 3.5 mm.

*Flower tube length.*—About 5 mm.

*Flower tube diameter, proximally.*—About 1 mm.

*Petals*.—Quantity per flower: Five petals in a single whorl; fused at the base. Lobe length: About 5 mm. Lobe width: About 4 mm. Lobe shape: Elliptic; occasionally reniform. Lobe apex: Obtuse. Lobe margin: Entire. Lobe texture, upper and lower surfaces: Smooth, glabrous; silky. Throat and tube texture: Smooth, glabrous; silky. Lobe color: When opening, upper surface: Close to 155A. When opening, lower surface: Close to 155A; distally, variably blushed with close to 181C. Fully opened, upper and lower surfaces: Close to NN155B. Throat color: Close to NN155B. Tube color: Close to NN155B.

*Sepals*.—Quantity per flower: Five small sepals in a single whorl; fused at the base; inconspicuous. Length: About 1 mm. Width: About 1 mm. Shape: Elliptic. Apex: Acute. Margin: Entire, ciliate. Texture, upper and lower surfaces: Smooth, glabrous. Color, fully opened, upper and lower surfaces: Close to 144C.

*Peduncles*.—Length: About 6 cm. Diameter: About 5 mm. Strength: Strong. Aspect: About 70° to 95° from the stem axis. Texture: Pubescent, pubescence canescent. Color: Close to 199C.

*Pedicels*.—Length: About 1 cm. Diameter: About 2 mm. Strength: Strong, somewhat flexible. Aspect: About 45° from peduncle axis. Texture: Pubescent, pubescence canescent. Color: Close to 199C.

*Reproductive organs*.—Androecium: Quantity per flower: About five. Filament length: About 2 mm. Filament color: Close to NN155B. Anther shape: Linear. Anther length: About 1 mm. Anther color: Close to 162B. Amount of pollen: Moderate. Pollen color: Close to 162B. Gynoecium: Quantity per flower: One. Pistil length: About 1 mm. Style length: About 1 mm. Style color: Close to 144C. Stigma shape: Peltate. Stigma color: Close to 175A. Ovary color: Close to 144C. Fruits: Length: About 1 cm. Diameter: About 6 mm. Texture: Smooth, glabrous. Color: Close to 202A.

Garden performance: Plants of the new *Viburnum* have been observed to have good garden and container performance and to tolerate rain, wind and to be suitable for USDA Hardiness Zones 4 through 7.

Pathogen & pest resistance: To date, plants of the new *Viburnum* have not been observed to be resistant to pathogens and pests common to *Viburnum* plants.

It is claimed:

1. A new and distinct *Viburnum* plant named 'SMNVCST' as herein illustrated and described.

* * * * *